United States Patent
Ford et al.

(10) Patent No.: US 8,436,296 B2
(45) Date of Patent: May 7, 2013

(54) FILTER WHEEL ASSEMBLY FOR DOWNHOLE SPECTROSCOPY

(75) Inventors: Jess V. Ford, Weatherford, TX (US); Sean M. Christian, Land O Lakes, FL (US); Dennis Roessler, Fort Worth, TX (US); Bryan W. Kasperski, Crowley, TX (US); Margaret C. Waid, Aledo, TX (US)

(73) Assignee: Precision Energy Services, Inc., Fort Worth, TX (US)

( * ) Notice: Subject to any disclaimer, the term of this patent is extended or adjusted under 35 U.S.C. 154(b) by 89 days.

(21) Appl. No.: 12/613,665

(22) Filed: Nov. 6, 2009

(65) Prior Publication Data

US 2011/0108721 A1    May 12, 2011

(51) Int. Cl.
    *G01V 5/08*    (2006.01)
(52) U.S. Cl.
    USPC ..................................................... 250/269.1
(58) Field of Classification Search ................. 250/268, 250/269.1–269.8, 252.1, 253–168, 345
    See application file for complete search history.

(56) References Cited

U.S. PATENT DOCUMENTS

| | | | | |
|---|---|---|---|---|
| 3,193,676 | A | * | 7/1965 | Smart ............................ 250/345 |
| 3,941,483 | A | * | 3/1976 | Ferrin ......................... 356/141.1 |
| 4,264,205 | A | | 4/1981 | Landa |
| 4,285,596 | A | | 8/1981 | Landa |
| 4,412,744 | A | | 11/1983 | Lee et al. |
| 4,525,627 | A | * | 6/1985 | Krempl et al. ................ 250/345 |
| 4,692,621 | A | * | 9/1987 | Passaro et al. ................ 250/343 |
| 4,785,806 | A | | 11/1988 | Deckelbaum |
| 4,832,490 | A | | 5/1989 | Boos |
| 4,962,815 | A | | 10/1990 | Schultz et al. |
| 4,968,148 | A | | 11/1990 | Chow |
| 4,994,671 | A | | 2/1991 | Safinya et al. |
| 5,128,797 | A | | 7/1992 | Sachse et al. |
| 5,166,747 | A | | 11/1992 | Schroeder et al. |
| 5,167,149 | A | | 12/1992 | Mullins et al. |
| 5,170,056 | A | | 12/1992 | Berard |
| 5,173,808 | A | * | 12/1992 | Auer et al. .................... 359/722 |

(Continued)

FOREIGN PATENT DOCUMENTS

| | | | |
|---|---|---|---|
| GB | 2391939 A | | 2/2004 |
| KR | 2002060005 A | * | 7/2002 |

(Continued)

OTHER PUBLICATIONS

Examiner's First Report in corresponding Australian Patent App. No. 2010227021, dated May 26, 2011.

(Continued)

*Primary Examiner* — Kiho Kim
(74) *Attorney, Agent, or Firm* — Wong, Cabello, Lutsch, Rutherford & Brucculeri, L.L.P.

(57) ABSTRACT

A downhole fluid analysis tool has a tool housing and a fluid analysis device. The tool housing is deployable downhole and has at least one flow passage for a fluid sample. The fluid analysis device is disposed in the tool housing relative to the flow passage. Inside the device, one or more sources generate a combined input electromagnetic signal across a spectrum of wavelengths, and a routing assembly routes generated signals into the reference and measurement signals. At least one wheel having a plurality of filters is rotated to selectively interpose one or more of the filters in the paths of the reference and measurement signals.

27 Claims, 7 Drawing Sheets

U.S. PATENT DOCUMENTS

| | | | |
|---|---|---|---|
| 5,257,086 | A | 10/1993 | Fateley et al. |
| 5,337,621 | A | 8/1994 | Spease |
| 5,371,543 | A | 12/1994 | Anderson |
| 5,401,966 | A | 3/1995 | Gray et al. |
| 5,440,118 | A | 8/1995 | Roscoe |
| 5,475,221 | A | 12/1995 | Wang |
| 5,504,575 | A | 4/1996 | Stafford |
| 5,557,398 | A * | 9/1996 | Wechsler et al. ............. 356/318 |
| 5,629,125 | A | 5/1997 | Leblans et al. |
| 5,825,478 | A | 10/1998 | Wilcox |
| 5,828,066 | A | 10/1998 | Messerschmidt |
| 5,859,430 | A | 1/1999 | Mullins et al. |
| 5,966,484 | A | 10/1999 | Yuuki |
| 6,064,488 | A | 5/2000 | Brand et al. |
| 6,075,595 | A | 6/2000 | Malinen |
| 6,128,078 | A | 10/2000 | Fateley |
| 6,301,959 | B1 | 10/2001 | Hrametz et al. |
| 6,388,251 | B1 | 5/2002 | Papanyan |
| 6,420,695 | B1 | 7/2002 | Grasdepot |
| 6,429,936 | B1 | 8/2002 | Scaduto |
| 6,437,326 | B1 | 8/2002 | Yamate et al. |
| 6,465,775 | B2 | 10/2002 | Mullins et al. |
| 6,476,384 | B1 | 11/2002 | Mullins et al. |
| 6,504,943 | B1 | 1/2003 | Sweatt et al. |
| 6,559,945 | B1 | 5/2003 | Grasdepot |
| 6,571,118 | B1 | 5/2003 | Utzinger et al. |
| 6,600,591 | B2 | 7/2003 | Anderson et al. |
| 6,678,050 | B2 | 1/2004 | Pope et al. |
| 6,693,701 | B2 | 2/2004 | Hansen |
| 6,753,960 | B1 | 6/2004 | Polynkin et al. |
| 6,768,105 | B2 | 7/2004 | Mullins et al. |
| 6,781,691 | B2 | 8/2004 | MacKinnon et al. |
| 6,798,518 | B2 | 9/2004 | DiFoggio et al. |
| 6,870,619 | B1 | 3/2005 | Tenhunen et al. |
| 6,939,717 | B2 | 9/2005 | Jiang |
| 6,995,360 | B2 | 2/2006 | Jones et al. |
| 7,013,723 | B2 | 3/2006 | Ramakrishnan et al. |
| 7,265,830 | B2 | 9/2007 | Wang |
| 7,279,678 | B2 | 10/2007 | Andrews et al. |
| 7,280,214 | B2 | 10/2007 | DiFoggio et al. |
| 7,321,428 | B2 | 1/2008 | Hunt |
| 7,336,356 | B2 | 2/2008 | Vannuffelen et al. |
| 7,360,924 | B2 | 4/2008 | Henson et al. |
| 7,362,422 | B2 | 4/2008 | DiFoggio et al. |
| 7,379,180 | B2 | 5/2008 | Vannuffelen |
| 7,403,680 | B2 | 7/2008 | Simbal |
| 7,508,506 | B2 | 3/2009 | Christian et al. |
| 7,609,380 | B2 | 10/2009 | Vannuffelen et al. |
| 7,782,389 | B2 | 8/2010 | Neidrich |
| 7,782,460 | B2 | 8/2010 | DiFoggio et al. |
| 2003/0206026 | A1 | 11/2003 | Diakonov et al. |
| 2004/0069942 | A1 | 4/2004 | Fujisawa et al. |
| 2004/0149915 | A1 | 8/2004 | Goncalves |
| 2004/0169858 | A1 | 9/2004 | Da Silva |
| 2004/0201850 | A1 | 10/2004 | Hajian et al. |
| 2004/0239923 | A1 | 12/2004 | Adams et al. |
| 2004/0239931 | A1 | 12/2004 | Teichmann et al. |
| 2005/0185179 | A1 | 8/2005 | Wang |
| 2005/0243312 | A1 | 11/2005 | Geshwind et al. |
| 2005/0275844 | A1 | 12/2005 | Kaltenbacher et al. |
| 2006/0243033 | A1 | 11/2006 | Freemark et al. |
| 2007/0013911 | A1 | 1/2007 | DiFoggio |
| 2007/0035737 | A1 | 2/2007 | Andrews et al. |
| 2007/0109537 | A1 | 5/2007 | Vannuffelen |
| 2007/0159625 | A1 | 7/2007 | DiFoggio |
| 2007/0171412 | A1 | 7/2007 | Vannuffelen |
| 2007/0171414 | A1 | 7/2007 | Vannuffelen |
| 2007/0229821 | A1 | 10/2007 | Christian et al. |
| 2008/0078544 | A1 | 4/2008 | Christian et al. |
| 2008/0087078 | A1 | 4/2008 | Vannuffelen |
| 2008/0165356 | A1 | 7/2008 | DiFoggio et al. |
| 2008/0173083 | A1 | 7/2008 | Kasperski et al. |
| 2008/0174777 | A1 | 7/2008 | Carron |

FOREIGN PATENT DOCUMENTS

| | | |
|---|---|---|
| WO | 81/00775 | 3/1981 |
| WO | 95/04263 | 2/1995 |
| WO | 2009126636 | 10/2009 |

OTHER PUBLICATIONS

European Search Report for Application No. EP 10188545, dated Feb. 14, 2011.

Cantrell, "The SLIM Spectrometer" Anal. Chem. 2003, 75, pp. 27-35, Department of Chemistry, Oregon State University, 153 Gilbert Hall, Corvallis, Oregon 97331-4001.

Hauser, "A Multi-Wavelength Photometer Based on Light-Emitting Diodes" Talanta, vol. 42, No. 4, pp. 605-612, 1995.

Malinen et al., Sensors and Actuators B 51 (1998) 220-224,"LED-based NIR spectrometer module for hand-held and process analyser applications," dated Jun. 16, 1998.

O'Toole, "Absorbance Based Light Emitting Diode Optical Sensors and Sensing Devices," Sensors 2008, 8, pp. 2453-2479; dated Apr. 7, 2008 obtained from www.mdpi.org/sensors.

Palma, "Portable light-emitting diode-based photometer with one-shot optochemical sensors for measurement in the field," dated Oct. 21, 2008, American Institute of Physics.

Schlumberger, "Fundamentals of Formation Testing," © 2006, pp. 1-5, 27-29, 55-67, 99-124, 199-202, Schlumberger Marketing Communications, Sugar Land, Texas, United States.

Schlumberger, "Engineering the Next-Generation Downhole Fluid Analysis Tool," dated May 7, 2007.

OZ Optics, "Silicon Optical Bench Platforms," dated Nov. 14, 2002, obtained from www.ozoptics.com.

Yeh, "A Low Cost LED Based Spectrometer," Journal of the Chinese Chemical Society, 2006, 53, pp. 1067-1072.

Frentress, "Field Photometer with Nine-Element Filter Wheel," dated Feb. 1964, vol. 3, No. 2, Applied Optics, pp. 303-308.

International Search Report and Written Opinion received in corresponding Application No. PCT/US07/82221, dated May 5, 2008.

International Search Report, International Patent Application No. PCT/US07/080112, mailed on Mar. 25, 2008.

Wagner, Eugene P. II, et al., "Construction and Evaluation of a Visible Spectrometer Using Digital Micromirror Spatial Light Modulation," Applied Spectroscopy, vol. 49, No. 11, 1995.

Ford, Joseph E., et al., "Dynamic Spectral Power Equalization Using Micro-Opto-Mechanics," IEEE Photonics Technology Letters, vol. 10, No. 10, Oct. 1998.

Duncan, Walter M., "Dynamic Optical Filtering in DWDM Systems Using the DMD," Solid State Electronics 46 (2002), pp. 1583-1585.

Lerner, J.M., et al., "The Optics of Spectroscopy—A Tutorial," Instruments SA, Inc., 1988.

Spudich, Thomas M., et al., "Potential for using a Digital Micromirror Device as a Signal Multiplexer in Visible Spectrscopy," Applied Spectroscopy, vol. 57, No. 7, 2003.

DeVerse, R. A., et al, "Realization of the Hadamard Multiplex Advantage Using a Programmable Optical Mask in a Dispersive Flat-Field Near-Infrared Spectrometer," Applied Spectroscopy, vol. 54, No. 12, 2000.

Badry, R., et al., "Downhole Optical Analysis of Formation Fluids," Oilfield Review, Jan. 1994.

Schroeder, R., "Slick Engineering," Spie's OE Magazine, May 2003.

Raghuraman, B., "Real-Time Downhold pH Measurement Using Optical Spectroscopy," SPE 93057, Society of Petroleum Engineers, 2005.

Sirkis, J., "Multifunctionality the Key in Challenging Instrumentation Markets," Lightwave Magazine, Mar. 2003.

Meyer, R., "RITMOS: A Micromirror-Based Multi-Object Spectrometer," Proceedings of the SPIE, 2004.

Smits, A.R., "In-Situ Optical Fluid Analysis as an Aid to Wireline Formation Sampling," SPE Formation Evaluation, Jun. 1995.

Texas Instruments, Application Report, "Single Panel DLP Projection System Optics," Mar. 2005.

Texas Instruments, Product Preview, "DMD 0.7 XGA 12.degree. LVDS DMD Discovery," Jul. 2005.

Texas Instruments, Product Preview Data Sheet, "DMD 0.7 XGA 12.degree. DDR DMD Discovery," Aug. 30, 2005.

Texas Instruments, "DMD Discovery 1100 Chip Set," 2004.
Texas Instruments, "DMD Discovery 3000 Digital Controller (DDC3000) Starter Kit Technical Reference Manual," Oct. 2005.
Texas Instruments, "DMD Discovery 1100 Controller Board and Starter Kit," Oct. 2004.
Texas Instruments, "DMD Discovery 1100 Controller Board GUI User's & Programmer's Guide," Sep. 2004, Unavailable.
Baker Hughes, " RCI Reservoir Characterization Instrument,"obtained from www.bakerhughesdirect.com, generated on Apr. 8, 2010.
Baker Hughes, "SampleView" 2000, obtained from www.bakerhughesdirect.com, generated on Apr. 19, 2010.
First office Action in co-pending U.S. Appl. No. 12/613,700, filed Jul. 8, 2011.
Reply to First Offince Action dated Jul. 8, 2011, in co-pending U.S. Appl. No. 12/613,700, filed Nov. 28, 2011.
Keränena, K., Blomberg, M., Tenhunena, J. And Kariojac, P., "Analytic and Raytrace Modeling of a Miniaturized Infrared Spectrometer Module," Technical Proceedings of the 2000 International Conference on Modeling and Simulation of Microsystems, pp. 660-663, dated 2000.

Thorlabs Inc., "Stepped Circular Neutral Density Filter," Drawing No. 10661-E01, Part No. NDC-100S-4, dated Jul. 20, 2006.
Thorlabs Inc., " Mounted Round Step Variable NDC Filter," Drawing No. 10664-E01, Part No. NDC-100S-4M, dated Jan. 10, 2007.
Dudley, Dana, et al., "Emerging Digital Micromirror Device (DMD) Applications," SPIE Proceedings vol. 4985, copyright 2003.
First Examination Report in counterpart Australian Appl. No. 20100227020, dated Jul. 22, 2011.
Notice of Allowance in co-pending U.S. Appl. No. 12/613,700, mailed Dec. 20, 2011.
First Examination Report in counterpart Australian Appl. No. 2010227019, dated Jul. 22, 2011.
First Examination Report in counterpart Canadian Appl. No. 2,718,452, dated Apr. 4, 2012.
First Examination Report in counterpart Canadian Appl. No. 2.725.359, dated Feb. 28, 2012.
Office Action in co-pending U.S. Appl. No. 12/613,808, mailed Nov. 7, 2012.

* cited by examiner

FILTER WHEEL ASSEMBLY FOR DOWNHOLE SPECTROSCOPY

CROSS-REFERENCE TO RELATED APPLICATIONS

This application is filed concurrently with application Ser. No. 12/613,700 entitled "Multi-Channel Source Assembly for Downhole Spectroscopy" and with application Ser. No. 12/613,808 entitled "Multi-Channel Detector Assembly for Downhole Spectroscopy" which are both incorporated herein by reference in their entireties.

BACKGROUND

Downhole tools use various types of sensors to test a downhole formation, analyze fluids, and perform other operations. Because the downhole environment has high temperatures, high pressures, harsh chemicals, and mechanical vibrations, the downhole tools must be mechanically designed to handle problems associated with such harsh conditions, and the downhole sensors must still be able to operate with analytical accuracy and reliability. Added to these challenges, the downhole sensors must fit in the limited space available in the downhole environment, must be light weight and power efficient, and have a large dynamic range. For these reasons, optical sensors are often the sensor of choice for downhole use.

In the art, spectrophotometers, spectrometers, spectrofluorometers, refractive index analyzers, and similar devices have been used to analyze downhole fluids by measuring the fluid's spectral response. Each of these device typically use some form of electromagnetic (EM) radiation to perform its function (i.e., to analyze the fluid). In general, the wavelengths of the EM radiation can be in the x-ray, gamma, ultraviolet, visible, infrared or any combination of these ranges. When the radiation is detected, the response can identify characteristics of the analyzed fluid, such as the type of fluid (e.g., oil, water, and/or gas), the level of filtrate contamination, the hydrocarbon composition (e.g., amount of methane (C1), ethane (C2), propane (C3), etc.), the gas-to-oil ratio (GOR), etc. Knowledge of these characteristics can then be employed to model the reservoir, plan production, and perform other tasks.

Typically, prior art optical devices have operational limitations in a downhole environment because of the manner in which the EM radiation must be split into various components. In addition, the number of measurement channels is limited due to the instrument design. These and other characteristics of prior devices typically result in limited capabilities for real-time, in-situ fluid analysis in a downhole wellbore environment. In any event, prior art optical devices have not incorporated dynamic real time referencing at each measurement wavelength to maintain sensor calibration, which could improve sensor performance.

For higher resolution, the optical devices are usually located at the surface to avoid the difficulties associated with the downhole environment. In these situations, fluid samples can be obtained downhole and transported to the surface for subsequent analysis. As expected, testing with this type of device does not provide prompt analysis. Alternatively, most of the electronic components of the optical device are located at the surface. Fiber optics running in the borehole carry input light from the surface component to a downhole sample. Then, fiber optics return the measurement light from the sample to the optical device's surface components so the measurement light can be analyzed. As expected, this type of device can be cumbersome and fragile and can usually only be employed in permanent installations.

Use of a filter wheel is one way to offer a number of spectral channels for analysis. For example, pharmaceutical and refining industries use filter wheel spectrometry/photometry to analyze fluids. In one example, a field photometer has a rotatable filter wheel with nine elements. See Z. Frentress, L. C. Young, and H. D. Edwards, "Field Photometer with Nine-Element Filter Wheel," Filter Wheel Art, Appl. Opt. 3, 303-308 (1964). In another example, a process photometer disclosed in U.S. Pat. No. 7,321,428 has a filter wheel with filters. Likewise, companies such as Turner Biosystems and Sherwood Scientific offer commercial filter wheel spectrometry systems for laboratory and industrial applications. However, such laboratory-based systems are not suitable for downhole use.

What is needed is an optical device that is deployed downhole to analyze fluids and that offers a high level of spectral reproducibility and reliability with a plurality of spectral channels. Furthermore, what is needed is an optical device with improved sensor performance that uses real time referencing to account for the harsh operating conditions found downhole.

SUMMARY

A downhole tool has a housing deployable downhole and has a flow passage for a fluid sample. A measurement device, such as a spectrometer, is disposed in the housing relative to the flow passage. The measurement device offers a high level of spectral resolution by providing a plurality of specific spectral channels—each having a relatively narrow spectral bandpass.

In operation, a source in the measurement device generates an optical signal across a spectrum of wavelengths. The source can have one or more light sources, including broadband sources, such as, but not limited to glow bars, metal halides, thermal emitters, light emitting diodes (LEDs), and super-luminescent light emitting diodes (SLEDs), etc. The source also has an optical routing assembly that either proportionally splits or temporally routes the beam using a scanning optical element into the measurement and reference channels.

From the source, a movable element or wheel having a plurality of filters distributed thereon selects the spectral wavelength distribution for the reference and measurement channels. These filters can be a substrate coated with material to produce a spectral distribution specified by a center wavelength and bandpass. A drive, such as one or more motors, is operable to rotate the wheel, and the wheel is rotatable to change which of the filters simultaneously filters both the reference and measurement channels. Although simultaneous changes for the filtering of the channels are preferred, they are not explicitly required. For example, sequential or time-delayed operation of the filtering changes can also be used if the necessary signal deconvolution is also used.

The wheel can have a selective orientation (i.e., clear channel) permitting unfiltered passage of the measurement and reference channels and can have another selective orientation (i.e., dark channel) completely restricting passage of the measurement and reference channels. In one implementation, the wheel has a substrate with filters coated onto the substrate and distributed about its axis. Alternatively, the wheel has a plurality of substrates affixed together and having filters coated thereon. In another alternative, the wheel can be a disc defining a plurality of openings distributed about the axis and having filters disposed therein. In yet another alternative, the wheel can use a plurality of wheels being separately rotatable. Each of these wheels can have a plurality of filters distributed about its axis of rotation.

DETAILED DESCRIPTION

A. Downhole Tool Having Measurement Device for Fluid Analysis

Figure 1:
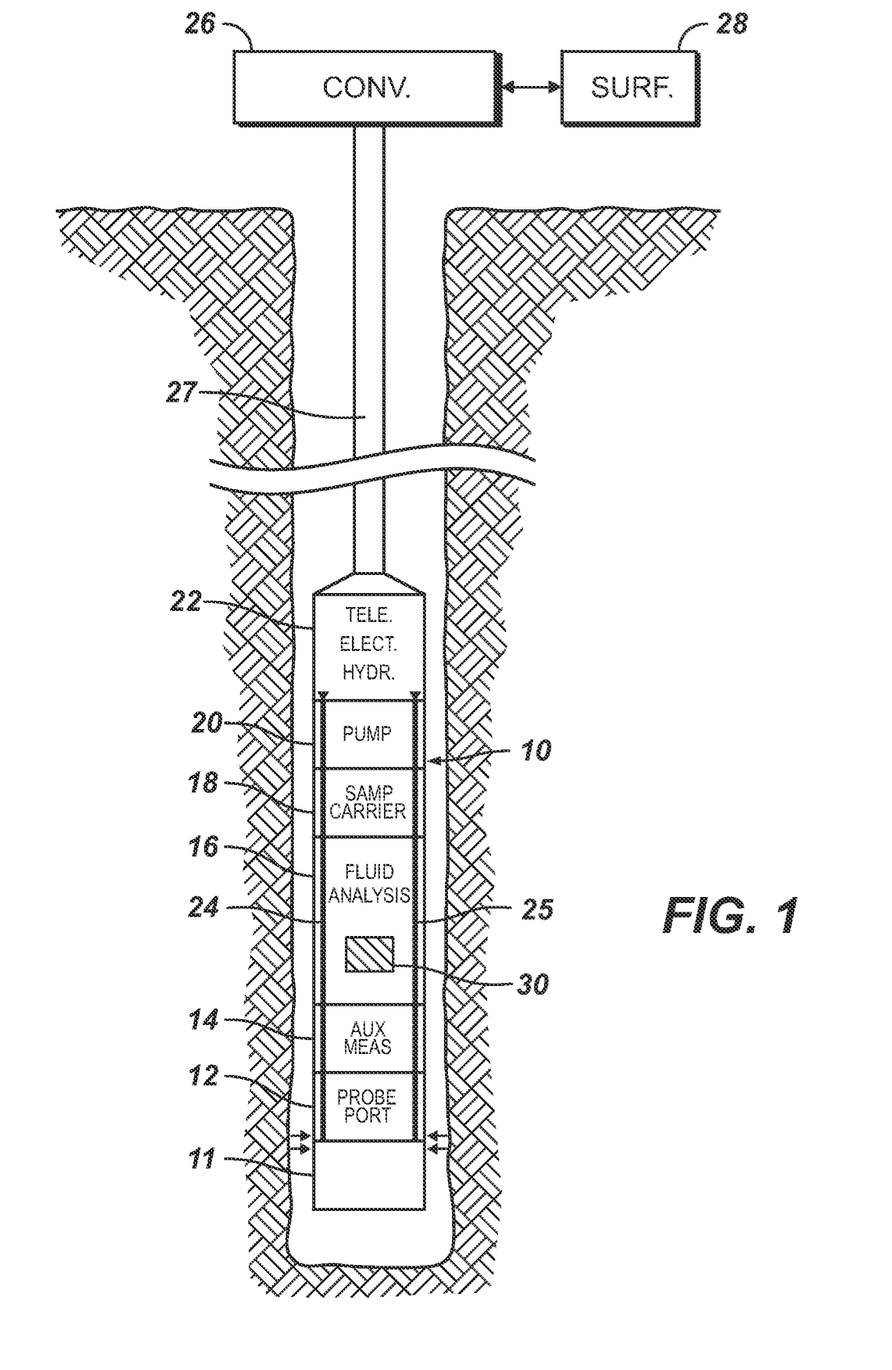
FIG. 1 illustrates a downhole tool having a measurement device for fluid analysis.

A downhole tool 10 in FIG. 1 has a measurement device 30 for in-situ sampling and analysis of fluids in a well. A conveyance apparatus 26 at the surface deploys the tool 10 downhole using a tubular, a cable, a wireline, or similar component 27. As shown in FIG. 1, the tool 10 can be a formation tester such as disclosed in U.S. Pat. Pub. No. 2008/0173083, filed 24 Jan. 2007, which is incorporated herein by reference. However, the measurement device 30 can be deployed in any suitable tool used for wireline formation testing, production logging, Logging While Drilling/Measurement While Drilling (LWD/MWD), or other operations.

1. Downhole Tool

As shown in FIG. 1, the formation tester tool 10 has dual fluid flow lines 24/25 that extend through sections of the tool 10 and that are functionally configurable. However, other types of formation tester tools could also be used, such as those having a single flow line. In operation, a probe 12 having an intake port draws fluid into the tool 10. To isolate the formation fluid samples from contaminates in the annulus, the tool 10 can use isolation elements, such as packers 11 or other devices, to isolate a region of the formation.

A pump 20 then pumps collected fluid from the probe 12 into the tool 10 via the flow lines 24/25. The fluid, which can contain hydrocarbon components (solid, liquid, and/or gas) as well as drilling mud filtrate or other contaminants, flows through the tool 10, and various instruments and sensors in the tool 10 analyze the fluid. For example, a measurement section 14 can have sensors that measure various physical parameters (i.e., pressure, temperature, etc.) of the fluid, and the measurement device 30 in the fluid analysis section 16 can determine physical and chemical properties of oil, water, and gas constituents of the fluid downhole. Eventually, fluid directed via the flow lines 24/25 can either be purged to the annulus or can be directed to the sample carrier 18 where the samples can be retained for additional analysis at the surface.

Additional components 22 of the tool 10 can hydraulically operate valves and other elements within the tool 10, can provide control and power to various electronics, and can communicate data via wireline or fluid telemetry to the surface. Uphole, surface equipment 28 can have a surface telemetry unit (not shown) to communicate with the downhole tool's telemetry components. The surface equipment 28 can also have a surface processor (not shown) that performs additional processing of the data measured by the tool 10.

2. Measurement Device for Downhole Fluid Analysis

As noted above, the fluid analysis section 16 uses the measurement device 30 for downhole fluid analysis. Depending on the configuration and types of sources and detectors used and their orientation relative to a sample, the measurement device 30 can operate as a photometric analyzer, reflectometer, spectroscope, spectrophotometer, spectrometer, or the like. For example, the measurement device 30 can operate as a multi-channel photometric analyzer in which discrete wavelengths are interrogated over a given measurement range. In common usage, such a multi-channel photometric analyzer can be referred to as a spectrometer. Thus, the measurement device 30 uses various discrete spectral channels to perform spectroscopic analysis of downhole fluid passing relative to it as the fluid is pumped through the tool 10 (FIG. 1). As such, the spectroscopic analysis discussed herein can include, but may not be limited to, analysis of transmission, absorbance, or both, and can apply chemometrics, derivative spectroscopy, and other techniques known in the art. Details of how a spectroscope can be implemented in a downhole tool are disclosed in U.S. Pat. No. 7,508,506, which is incorporated herein by reference.

Figure 2A:
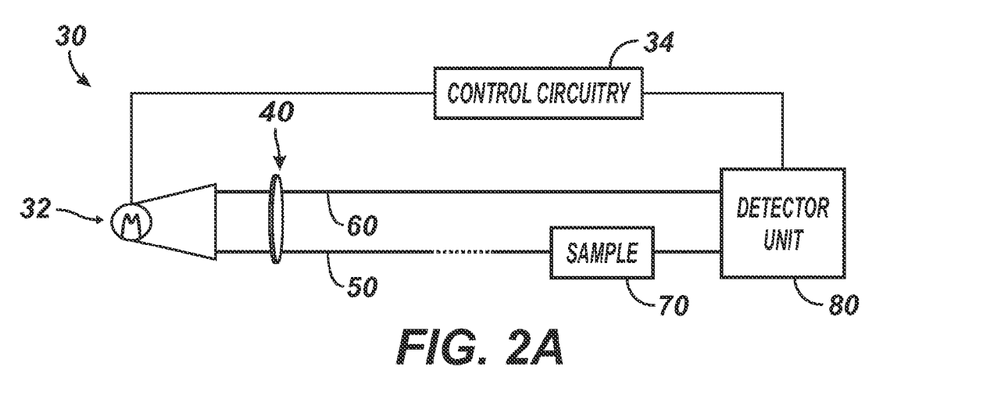
FIG. 2A schematically illustrates a measurement device for fluid analysis having a source unit, a selective filter unit, a sample unit, and a detector unit.

As schematically shown in FIG. 2A, the measurement device 30 has a source unit 32, source control circuitry 34, a wavelength selection unit 40, a sample assembly 70, and a detector unit 80. The device 30 uses signals from the source unit 32, filters the signals with the wavelength selection unit 40, passes the measurement channel to the fluid sample with the selected wavelength using the sampling assembly 70, and detects the optical signals with the detector unit 80 to determine various characteristics of the sample fluid.

Figure 2B:
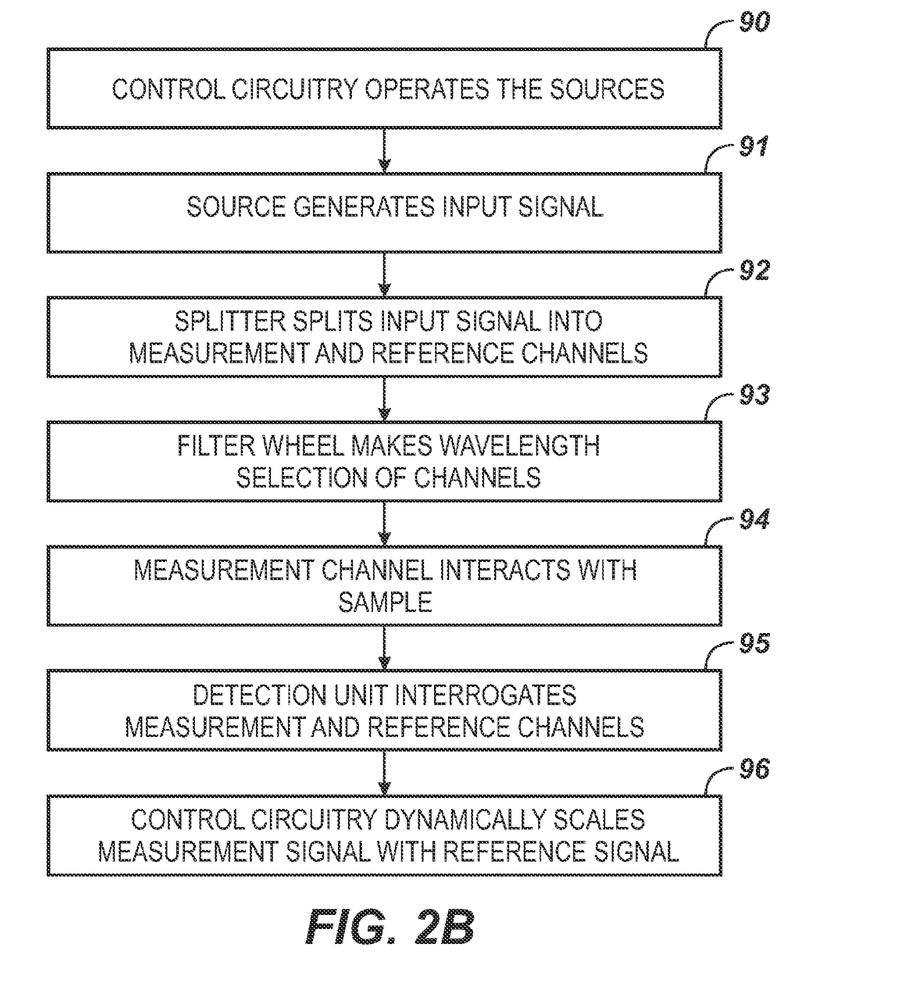
FIG. 2B shows the general operation of the measurement device shown in FIG. 2A.

Referring concurrently to FIG. 2B, the source control circuitry 34 operates the source unit 32 (Block 90) to generate an input signal with the one or more sources in the source unit 32 (Block 91). In general, the source unit 32 provides a broadband source so that the generated optical signal (EM radiation) from the unit 32 preferably has a broad wavelength distribution. In general, the source unit 32 can use various types of sources, such as continuous broadband sources (i.e., halogen lamps), although a combination of other sources, such as light emitting diodes (LEDs), laser diodes (LDs), glow bars, etc., could be used. In one implementation, for example, the source unit 32 can have one broadband source, such as a tungsten halogen lamp, deuterium light source, short arc Xenon light source, coiled filament IR emitter, arc lamp, metal halide lamp, etc. In another implementation, the source unit 32 can be a multi-channel source assembly as disclosed in co-pending application Ser. No. 12/613,700 entitled "Multi-Channel Source Assembly for Downhole Spectroscopy," which has been incorporated herein in its entirety.

The source unit 32 routes the input signal into a measurement channel 50 and a reference channel 60 (Block 92). For example, a splitter or other device in the source 32 splits the input signal into the separate channels 50 and channel 60. Throughout this disclosure, these channels 50/60 or light paths are referred to as a "measurement channel" and a "reference channel" to indicate that the measurement channel 50 interrogates a sample with EM radiation while the reference channel 60 is used for reference. Although one measurement channel 50 is shown along with one reference channel 60, it will be appreciated that multiple measurements channels 50 can be provided for the same reference channel 60. Therefore, the device 30 can have several measurement channels 50 along with sample assemblies 70 and detector units 80 for separate analysis.

From the source unit 32, the channels 50 and 60 pass through the wavelength selection unit 40, which selects the wavelength(s) for the channels 50/60 (Block 93). As detailed below, the wavelength selection unit 40 can include one or more movable elements for moving filters relative to the channels 50/60. For example, the one or more movable elements can be filter wheels rotatable about an axis of rotation. These filter wheels can having bandpass filters for filtering the optical signals passing therethrough and transmitting these optical signals with a specific wavelength distribution (commonly called a waveband, bandwidth, or bandpass). Leaving the wavelength selection unit 40, the wavelength selected measurement channel 50 interacts with a sample fluid via the sample unit 70 (Block 94). For its part, the sample unit 70 can use different designs, including, but not limited to, a reflectance accessory, a transmittance accessory, a fluorescence accessory, an Attenuated Total Reflectance (ATR) accessory, or any other sampling or monitoring device known to those skilled in the art.

After interaction with the sample, the measurement channel 50 is detected by the detector unit 80 for analysis (Block 95). Concurrent with the interrogation of the filtered measurement channel 50, the filtered reference channel 60 is also interrogated (Block 95). To do this, the detector unit has at least one measurement detector (not shown) and at least one reference detector (not shown) to detects spectral signals of the measurement channel 50 and the reference channel 60, respectively. In general, the detectors in the unit 80 can cover the required spectral bandwidth provided and can use any of the various available detector materials (i.e., Si, InGaAs, PbS, PbSe, MCT, etc.) and any of the various available configurations (i.e. photodiodes (PD), avalanche photodiodes (APD), photomultiplier tubes (PMT), Multi-Channel Plates (MCP), etc.). Details of the detector unit 80 are disclosed in co-pending application Ser. No. 12/613,808 entitled "Multi-Channel Detector Assembly for Downhole Spectroscopy," which has been incorporated herein in its entirety.

At this point, the control circuitry 34 can uses the detected signals to dynamically scale the measurement channel 50, to control the wavelength selection unit 40, and to perform other operations disclosed herein. For example, the control circuitry 34 can dynamically scale the measurement channel 50's signal by the reference channel 60's signal to account for downhole conditions, drift, or the like (Block 96).

Once the received signals are scaled and decoded, the resulting spectral data can be used to determine chemical and/or physical properties of the sample fluid. This can be performed by the control circuitry 34 used to control the source unit 32/filter unit 40 or by some other controller. Ultimately, as referenced above, the measurement device 30 in FIG. 1 can transmit spectral data to a processing system (not shown) located within the tool 10 or at the surface equipment 28.

B. Downhole Measurement Device

Figure 3A:
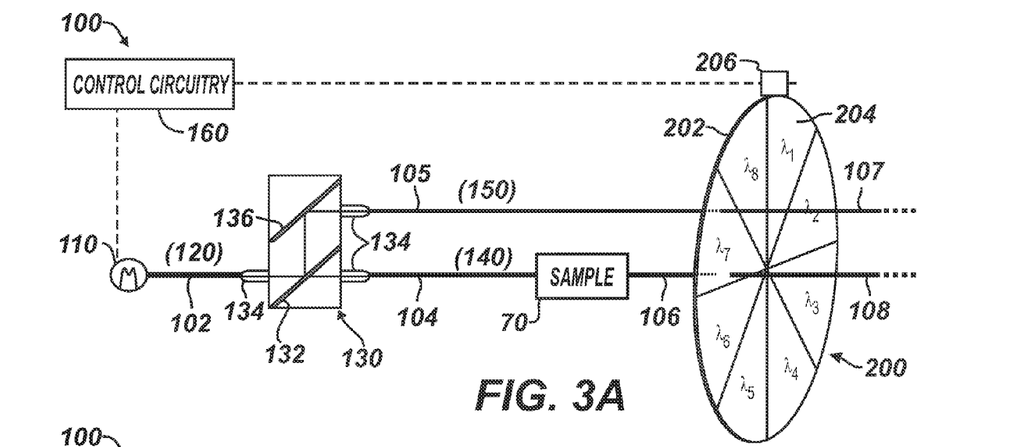
FIG. 3A illustrates a first arrangement of a measurement device having a selective filter unit, a beam-splitter unit, and control circuitry.
Figure 3B:
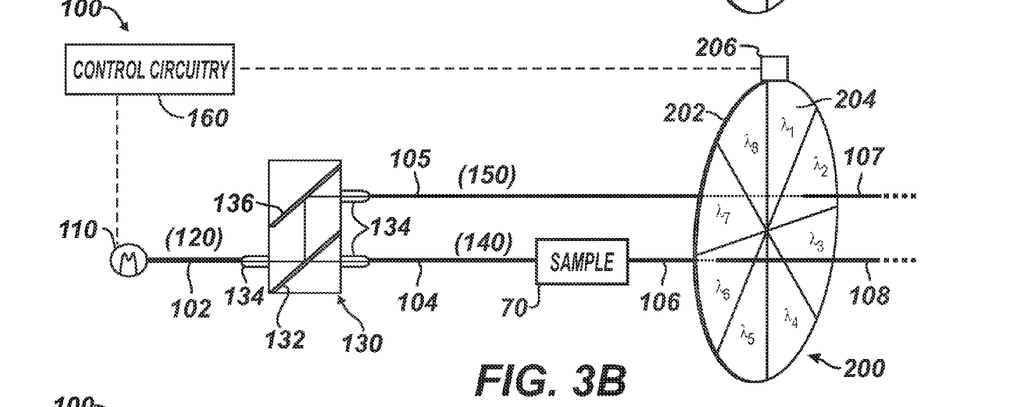
FIG. 3B illustrates a second arrangement of a measurement device having a selective filter unit, a beam-splitter unit, and control circuitry.

With an understanding of the measurement device 30 and the downhole tool 10 in which it can be deployed, discussion now turns to FIGS. 3A-3B showing different arrangements of a measurement device 100 for downhole spectroscopy according to certain teachings of the present disclosure.

1. First Arrangement

In a first arrangement shown in FIG. 3A, the measurement device 100 has a source unit 110, a router unit 130, control circuitry 160, and a selective filter unit 200. As discussed above, the source unit 110 can have one or more light sources (not shown) to provide a broadband source. The control circuitry 160 controls the source(s) in the unit 110, and the unit 110 optically couples the generated signals of the source(s) to an input channel 120, which may be carried by an individual fiber optic cable, a fiber optic bundle, or other device 102 as shown in FIG. 3A. The channel 120 may also use any beam routing methodology known to those versed in the art, such as through space optics using reflection, diffraction, waveguides, etc.

At the router unit 130, an optic (e.g., a collimator) 134 collimates the input channel 120, and a fractional beam splitter 132 then creates fractional beam intensity along separate optical paths to produce two separate channels—a measurement channel 140 and a reference channel 150. Splitting the input channel 120 in this way provides a means for real time scaling of the measurement channel with the reference channel. This configuration improves measurement accuracy, reproducibility, and stability through removal of light source variability due to environmental effects.

As shown, the splitter 132 creates a first optical path constituting a first fraction or majority of the input channel 120. This first optical path passes through an optic 134 to a fiber optic 104 for the measurement channel 140. The splitter 132 also creates a second optical signal constituting a second fraction or minority of the input channel 120. This second optical path passes from the splitter 132 to an integrated reflector 136 that directs the optical signal through another optic 134 and into a fiber optic 105 for the reference channel 150. The reflector 136 is not required, as other routing schemes could be used. In one implementation, the measurement channel 140 constitutes 90% of the input channel 120, while the reference channel 150 constitutes 10% of the input channel 120, although other percentages could be used in other implementations.

The measurement channel 140 passes from the router unit 130 to the sample unit 70 where the channel 140 interacts with a sample. After interacting with the sample fluid, the measurement channel 140 is carried by a fiber optic 106 to the selective filter unit 200. In contrast to the input fiber optic 104 which can be a 400-micron core fiber optic cable, this output fiber optic 106 can be a 600-micron core fiber optic cable in one implementation. In general, the output fiber optic 106's core diameter could be equivalent to or larger than that of the input fiber optic 104 depending on the particular sample unit 70 used. The asymmetry between the input and output fiber optics 104/106, however, maximizes the sample unit (70)'s throughput over the entire range of downhole environmental conditions.

Ultimately, the output fiber optic 106 delivers the measurement channel 140 to the selective filter unit 200. As shown, the filter unit 200 has a wheel 202 with a plurality of filters 204. The measurement channel 140 passes through one or more of the filters 204 on the wheel 202 after the measurement channel 140 has passed through the sample unit 70. After traversing the filter unit 200, the wavelength selected measurement channel 140 passes to another fiber optic 108 that can carry the signal to a measurement detector unit (not shown) for detection and analysis.

The filters 204 on the wheel 202 each have a spectral bandwidth suitable for analyzing the fluid specific to the process under measurement. In addition, the filter unit 200 can have a clear channel and a dark channel for spectral scaling. Although one filter wheel 202 is shown, the filter unit 200 can also use multiple wheels as discussed later to reduce the complexity of having an individual wheel while still allowing for a large number of optical channels.

Also from the router unit 130, the second optical path constituting the minority of the input channel 120 for the reference channel 150 is directed to the filter unit 200 via a fiber optic 105. As shown in FIG. 3A, the router unit 130 can direct the reference channel 150 using the reflector 136, such as a mirror or prism. In this way, the fiber optics 104/105 carrying the two channels 140/150 can be positioned adjacent and parallel to one another and conserve space in the measurement device 100 used downhole.

After the router unit 130, the reference channel 150 carried by the fiber optic 105 passes to the filter unit 200. For correlation between the measurement and reference channels 140/150, both channels 140/150 pass through the same filter 204 at the same time. After traversing the filter unit 200, the wavelength selected reference channel 150 passes to another fiber optic cable or assembly 107 that can eventually couple to a reference detector unit (not shown) for detection and analysis.

2. Second Arrangement

In a second arrangement shown in FIG. 3B, the measurement device 100 has a source unit 110, a router unit 130, control circuitry 160, and a selective filter unit 200, which have a similar arrangement to that discussed previously. Again, the splitter 132 splits the input channel 120 into a measurement channel 140 and a reference channel 150, the measurement channel 140 interacts with a sample via sample assembly 70, and the channels 140 and 150 pass to the filter unit 200. In contrast to the previous arrangement, the measurement channel 140 passes through filters 202 on the wheel 202 out of phase from the reference channel 150. Although shown here as being 180-degrees out of phase, other configurations could be used. After traversing the filter unit 200, the wavelength selected signals from the measurement and reference channels 140/150 pass a detector unit (not shown) for detection and analysis the out of phase signals.

3. Third Arrangement Having Scanning Optic

Figure 3C:
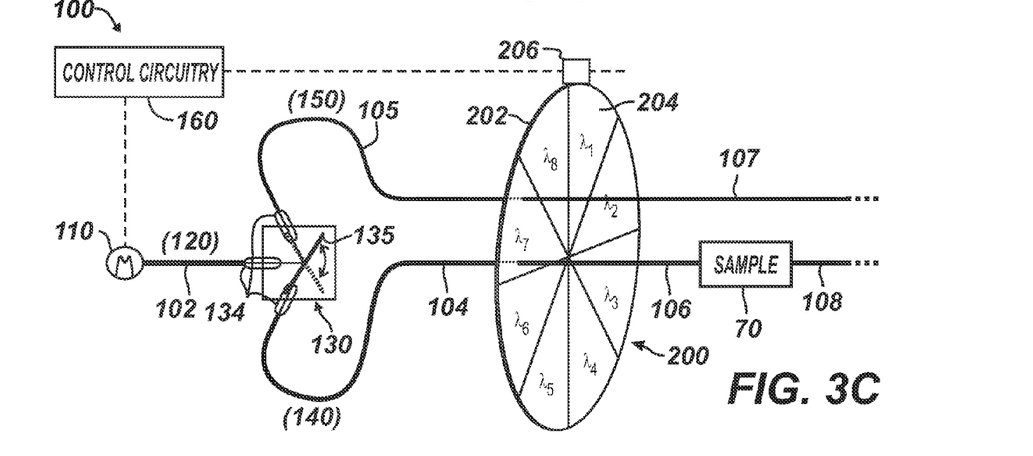
FIG. 3C illustrates a third arrangement of a measurement device having a selective filter unit, an adaptive optical element, and control circuitry.

In a third arrangement shown in FIG. 3C, the measurement device 100 again has source unit 110, router unit 130, control circuitry 160, and selective filter unit 200. Generating of the input channel 120 can follow the same course as discussed previously. In contrast to the previous arrangement, however, the router unit 130 uses an adaptive optical element or scanning optic 135 (as opposed to the splitter 132 as in FIGS. 3A-3B) to split the input channel's optical signal into separate channels 140/150. The scanning optic 135 can be a scanning mirror, such as a micro-electro-mechanical (MEM) mirror device or a Micro-Electro-Mechanical System (MEMS) scanning mirror. Suitable MEMS scanning mirrors are available from Electro-Optical Products Corporation (EOPC) and Hiperscan. Details of using a scanning optic are disclosed in U.S. Pat. No. 7,508,506, which has been incorporated herein by reference in its entirety.

In use, an optic 134 at the router unit 130 collimates the input channel 120 generated by the source unit 110 and carried by fiber optic 102. Then, the scanning optic 135 splits the input channel 120 by serially directing all of the input channel 120 at two other optics 134 relative to the scanning optic 135. In general, the input channel 120's signal incident on the scanning optic 135 can be manipulated to improve its shape, dispersion, or intensity using various available optics not shown for simplicity. In addition, the scanning optic 135's orientation is controlled via a controller—either independent from or integrated into the control circuitry 160.

In one orientation, for example, the scanning optic 135 directs all of the input channel 120 to an optic 134 and a fiber optic 104 for the measurement channel 140. Once oscillated or rotated, the scanning optic 135 then directs all of the input channel 120 to an optic 134 and a fiber optic 105 for the reference channel 150.

Further in contrast to previous arrangements, the selective filter unit 200 positions before the sample unit 70 in the path of the measurement channel 140. This position can be used if the device 100 uses mechanical chopping of the input channel 110 for frequency modulation. Use of the scanning optic 135 may be able to achieve this mechanical chopping. In other arrangements, a chopper wheel (not shown) driven by a chopper motor (not shown) can be positioned in the path of the input channel 120 from the source unit 110 to modulate the input signal at a desired frequency. Alternatively, a chopper wheel (not shown) can be incorporated into the selective filter unit 200 to mechanically modulate the two channels 140/150. Furthermore, sources in the source unit 110 can be electrically modulated by the control circuitry 160.

In FIGS. 3A-3C, three arrangements for the measurement device 100 have been shown. It will be appreciated with the benefit of the present disclosure that other arrangements are possible and that components from one of the disclosed arrangements can be exchanged or combined with those of another arrangement, as well as with any other components or arrangements disclosed herein or known to those versed in the art. Moreover, although fiber optics have been shown, it will be appreciated that other beam routing methodologies known to those versed in the art can be used, such as space optics using reflection, diffraction, waveguides, etc.

C. Modular Housing

Figure 4A:
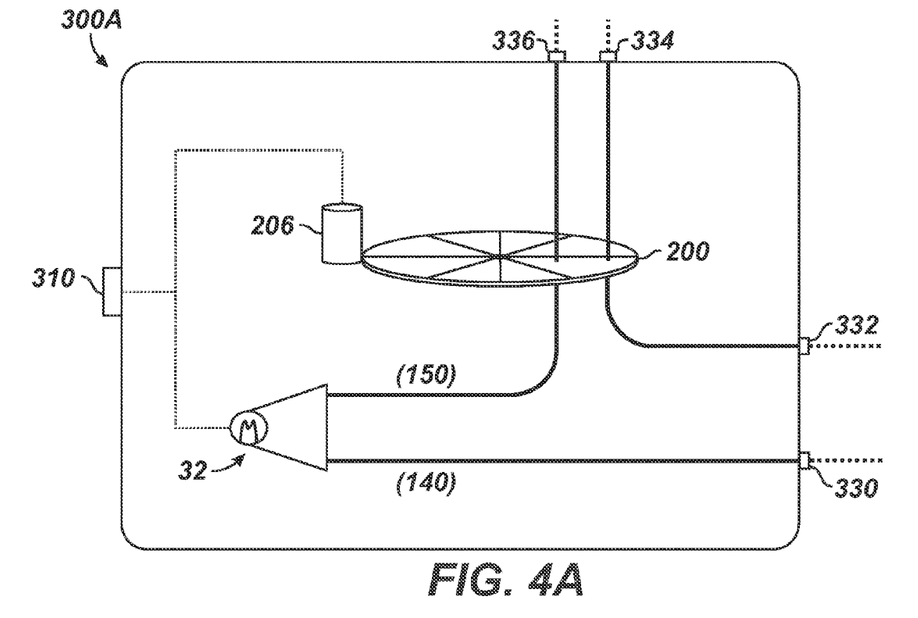
FIGS. 4A-4B illustrate housing arrangements for the disclosed measurement device.
Figure 4B:
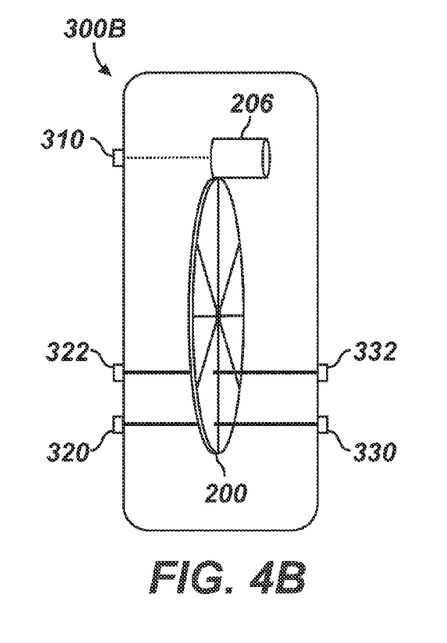

FIGS. 4A-4B illustrate housing arrangements for the measurement device 100 disclosed herein. Because the measurement device 100 is used downhole, housing its components can be constrained by the available tool space and the downhole environmental specifications. Ideally, components of the measurement device 100 have a housing that is amenable to downhole deployment and that can fit into the tight downhole space required in a downhole tool. Therefore, the measurement device 100 is preferably constructed as a discrete modular unit that can be incorporated or connected to other modular units for sampling and detection in a downhole tool.

In one example, a housing 300A contains the source unit 32 and the selective filter unit 200 with drive 206. The housing 300A has an electrical connector 310 for coupling the housing 300A to power and control sources (not shown). Optical signals from the source unit 32 are split into the measurement and reference channels 140/150 as discussed previously. The reference channel 150 passes through the filter unit 200 to an optical connector 336 for passage to a detector unit (not shown).

For the measurement channel 140, an output optical connector 330 couples the measurement channel 140 to a sample assembly (not shown) using fiber optics or the like, and an input optical connector 332 receives the measurement channel 140 after interaction with the sample fluid. After the returned measurement channel 140 passes through the filter unit 200, another output optical connector 334 couples the channel 140 to a detector unit (not shown) using fiber optics or the like.

In another example shown in FIG. 4B, a housing 300B only contains the selective filter unit 200 and drive 206. The unit's drive 206 couples to control electronics with electrical connector 310, as before. Optical connectors 320, 322 receive the measurement and reference channels (140/150) and pass them to the filter unit 200. On the other side of the unit 200, an output connector 330 carries the measurement channel (140) to a sample unit (not shown) and a measurement detector (not shown), as discussed previously, that are housed separate from the current housing 300B. Likewise, an output connector 332 carries the reference channel (150) to a reference detector (not shown), as discussed previously, that is also housed separately.

Even though the housings in FIGS. 4A-4B have been described above with reference to some of the components of the disclosed device 100 in FIGS. 3A-3B, it will be appreciated that additional housing arrangements can be provided using other components of the device 100 disclosed herein or known to those versed in the art.

D. Selective Filter Unit

Figure 5:
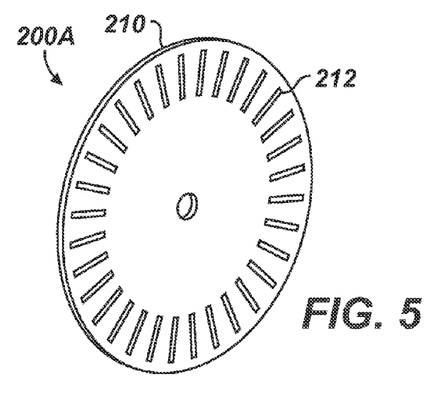
FIG. 5 illustrates a filter wheel having a disc with optic filters disposed therein.

The selective filter unit 200 disclosed above can be constructed in a number of ways. In one implementation shown in FIG. 5, a filter wheel unit 200A can be constructed as a solid disc or wheel 210 composed of a suitable metal or other material. From an opto-mechanical standpoint, the solid wheel 210 should be properly balanced for rotation when used. The solid wheel 210 can be constructed with a plurality (typically 2-32) of optic filters 212 disposed in slots, holes, or other openings arranged around the wheel 210. These openings can be rectangular, circular, or other shape. However, because both the measurement and reference channels (140/150) are filtered through the same optic filter 212 at the same time, the filters 212 are preferably sized and shaped to allow for passage of both channels while still fitting all the desired number of filters on the wheel 200A.

Figure 6:
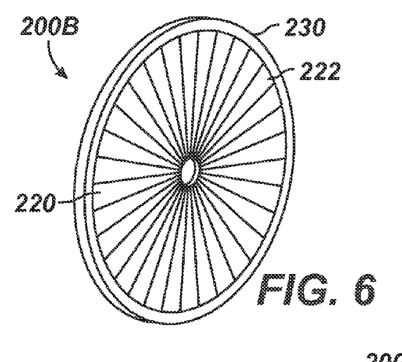
FIG. 6 illustrates a filter wheel having a substrate coated with wavelength selective material(s).

In another implementation shown in FIG. 6, a filter wheel unit 200B has a single filter wheel substrate 220 having a plurality (i.e., 2-32) of filters 222 coated thereon. The substrate 220 can be composed of fused silica, glass, borosilicate crown glass, sapphire, quartz, or other suitable material, and the individual filters 222 can be coatings of metal, metal oxides, or other suitable material. The substrate 220 can use a surrounding metallic rim 230 at its periphery and can use central washers and other mounting components (not shown) for mounting on a central rotation rod.

Figure 7A:
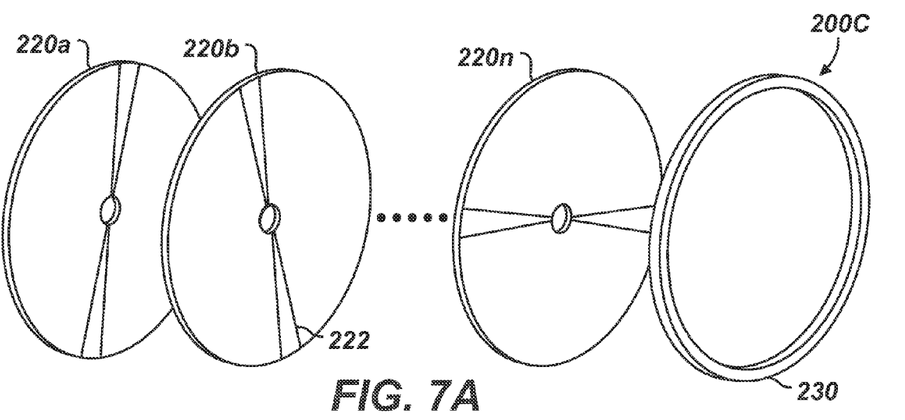
FIG. 7A illustrates a number of substrates having filter coatings and combinable together to form a filter wheel.

To simplify manufacture, a filter wheel unit 200C in FIG. 7A uses a number of thin substrates 220a-n constructed of a suitable substrate material. Each of the substrates 220a-n is coated with filters 222 at opposing arcs around the substrate. The coated substrates 220a-n are then assembled using optical cement into a wheel that has all of the desired wavelengths of filter coatings interleaved with one another. Again, this wheel 200C can have a surrounding rim 230 and central mounting components (not shown).

Figure 7B:
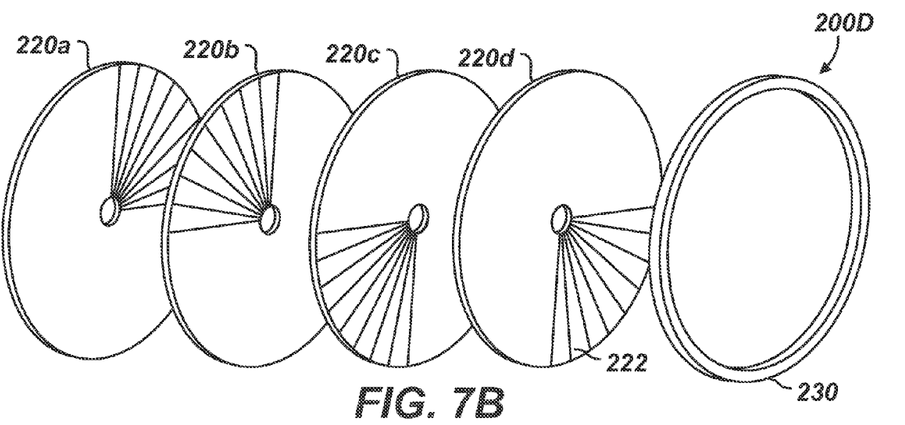
FIG. 7B illustrates four substrates having filter coatings and combinable together to form a filter wheel.

As an alternative, a filter wheel unit 200D shown in FIG. 7B has four thin substrates 220a-d constructed of a suitable substrate material. Each of the substrates 220a-d is coated with about six (6) filters 222—all positioned within one of the substrate's quadrants. These coated substrates 220a-d are then assembled using optical cement into a wheel that has all of the desired wavelengths of filter coatings. Again, this wheel 200D can have a surrounding rim 230 and central mounting components (not shown).

Figure 8A:
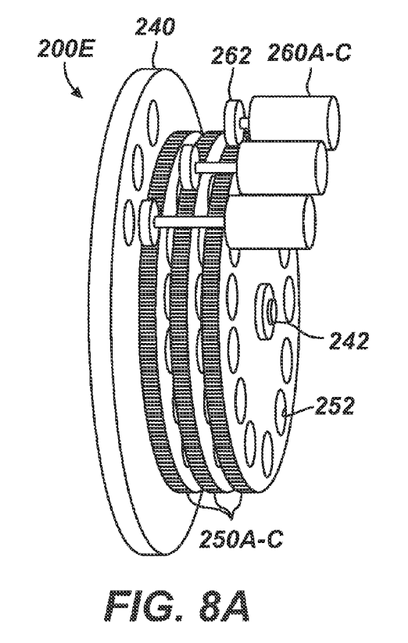
FIG. 8A-8C illustrate a filter wheel unit having a plurality of separate wheels.
Figure 8B:
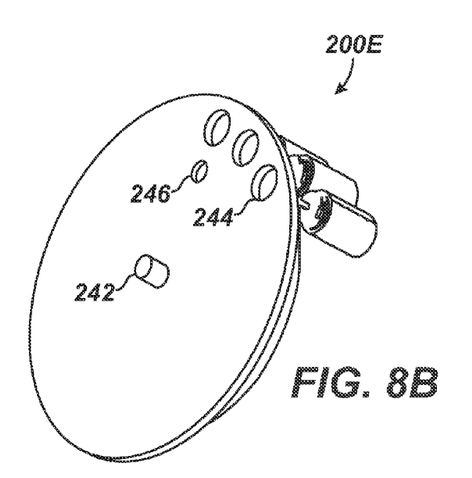
Figure 8C:
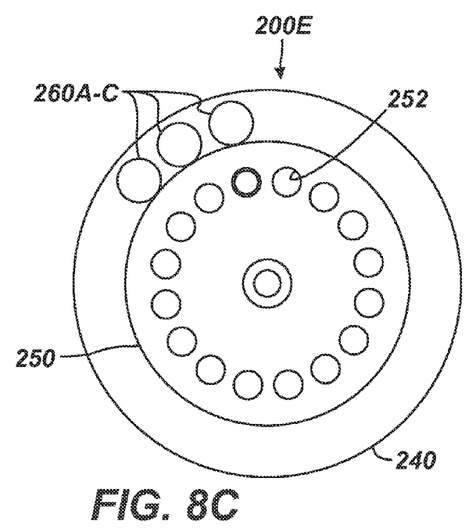

In an alternative shown in FIGS. 8A-8C, a filter wheel unit 200E can use several separate wheels 250A-C constructed for rotation on a base 240. As shown in FIG. 8A, the base 240 is flat and circular, and a rotation shaft 242 extends from the center of the base 240. Near its periphery, the base 240 has several holes 244 to accommodate drive components as discussed below. Also close to the base's perimeter as best shown in FIG. 8B, the base 240 has an aperture 246 through which the beams of the reference and measurement channels pass from the device's other components (not shown).

The separate wheels 250A-C are rotatable on the shaft 242. In the present example, three wheels 250A-C are shown, but two or more wheels could be used depending on the implementation and the number of desired wavelengths to be selected. As will be appreciated, any suitable form of bearings, spacers, and the like can be used to allow the dials 250A-C to remain balanced and rotate on the shaft 242. As shown, the motion and speed of each wheel 250A-C is controlled by an individual stepper motor 260A-C coupled to the wheel 250A-C by gearing or the like. Alternatively, one stepper motor with appropriate gearing for each dial 250A-C could be used.

Each of the wheels 250A-C has a plurality of holes 252 formed symmetrically near the peripheral edge. For example, wheels 250A-C can have from 2 to 16 holes 252. These holes 252 hold optical filters of sufficient size for both the measurement (140) and reference channels (150) to pass through for wavelength selection. Because the various holes 252 on wheels 250A-C include optical filters therein, different optical filtering can be achieved depending on the orientation of the three wheels 250A-C and the alignment of their separate holes 252 relative to one another.

For example, one or more of the wheels 250A-C can have one or more holes 252 without an optical filter. In this way, selective orientation of the wheels 250A-C permits unfiltered passage of the measurement and reference channels through one, two, or all of the dials 250A-C. In addition, different optical filtering can be achieved through overlapping filters of one, two, or three of the wheels 250A-C at the same time depending on their selective orientation. In addition, one or more of the wheels 250A-C may have holes 252 or portions (i.e., lack of holes) that are "dark" so that the wheels 250A-C can chop the signals for frequency modulation and to provide a "dark" signal for real time dark current correction (referencing). In addition, the filter wheel unit 200E can incorporate a chopper assembly to modulate the optical signals for lock-in detection.

Figure 9:
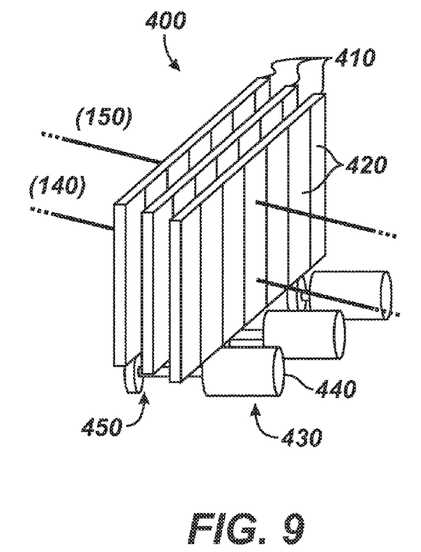
FIG. 9 illustrates another selective filter unit according to the present disclosure.

Although the movable element for selectively moving filters relative to the channels has been primarily described as one or more wheels rotatable about an axis, other forms of movable elements could be used. As shown in FIG. 9, for example, a selective filter unit 400 has movable elements composed of several plates 410. Although several plates 410 are shown, the unit 400 could have only one such plate 410. Each plate 410 can be a substrate having filters 420 coated thereon. Alternatively, each plate 410 can be a solid component having windows for holding individual filters 420.

A drive 430 having one or more motors 440 and gearing (such as rack and pinion gears) 450 moves or oscillates the plates 410 back and forth to alter the alignment and arrangement of filters 420 relative to the channel signals 140/150 passing through the plates 410. Spaces in the plates 410 may lack a filter, allowing the channel signals 140/150 to pass through that particular plate 410 unfiltered to the next adjacent plate 410. Manipulating the various plates 410 and arranging the various filters 420 with the drive 430 can thereby produce a plurality of selective filterings for the channel signals 140/150 similar to those achieved with the filter wheels discussed previously.

E. Control Circuitry

Figure 10:
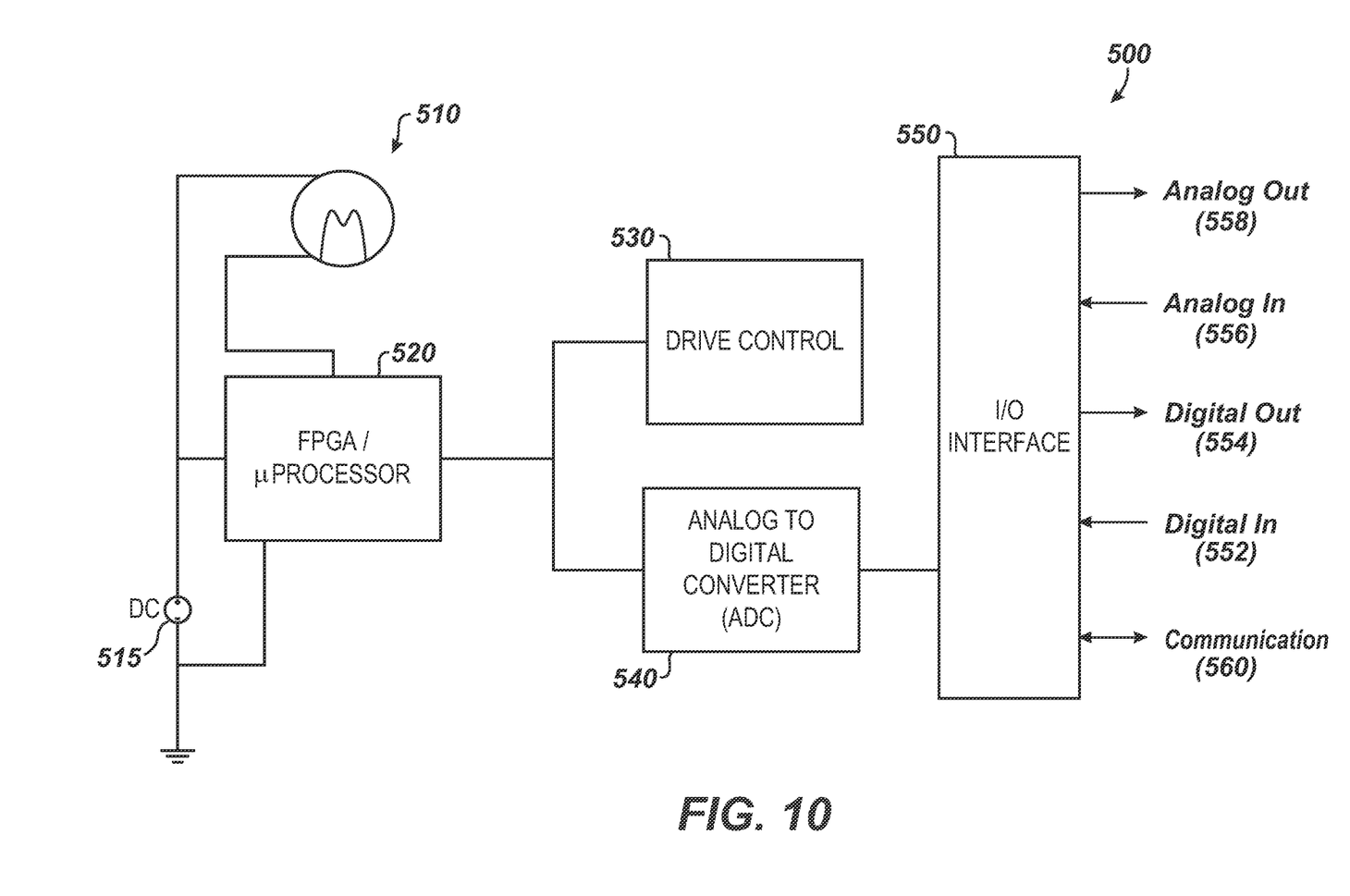
FIG. 10 schematically illustrates control circuitry for the disclosed measurement device.

As discussed previously in FIG. 3A-3C, the measurement device 100 uses control circuitry 160 to control the source(s) in the source unit 110 and to control the selective filter unit 200. FIG. 10 schematically illustrates one embodiment of control circuitry 500 for the disclosed device. The control circuitry 500 has processing circuitry 520 coupled to a source 510, drive control circuitry 530, conversion circuitry 540, and an input/output interface 550. As noted previously, the source 510 can have one or more sources, including one broadband source (halogen lamp), a combination of a broadband source and discreet sources (e.g., LEDs), etc. As shown here, the source 510 is a single broadband source according to one embodiment, but other sources as disclosed herein could be used.

The processing circuitry 520 uses programmable control schemes to control operation of the source 510 and selective filter assembly (not shown) and can have a microprocessor or Field-Programmable Gate Array (FPGA). In operation, the processing circuitry 520 drives the source 510 and performs other control functions discussed below.

To drive the source 510, the processing circuitry 520 controls the power from a DC power source 515 to the source 510 using control signals communicated to transistors or the like (not shown). In driving the source 510, the intensity can be controlled by the processing circuitry 520 so that the intensity can be modified if desired, or the intensity can be fixed by the control circuitry 500's hardware. In driving the source 510, the processing circuitry 520 can also use frequency modulation and other techniques disclosed herein.

The processing circuitry 520 also controls the selective filter wheel (See e.g., FIGS. 5-8B) by coupling to a drive control 530 for operating the one or more motors of the device's filter wheel unit (not shown). The drive control 530 can use conventional circuitry for operating one or more suitable motors, such as stepper motors or the like. The input/output interface 550 has digital and analog inputs 552/556 to receive data and has outputs 554/558 to send data and can have another other form of communication interface 560. As one example, the analog output 558 can be used to send signals to another downhole controller or to send signals to a telemetry unit to relay to surface equipment. For this reason, the control circuitry 500 may include a digital-to-analog conversion circuit (not shown).

In another example, the analog input 556 can receive analog signals that externally control the circuitry's operation. The external control can also operate the control circuitry 500 to handle events that require exact timing. For example, trigger signals at the digital output 552 and input 554 of the interface 550 can be used for external control. In either analog or digital, the external control can be manual or automated and can be from an external controller, such as surface equipment, or from a separate downhole controller (i.e. from the detection control unit as described co-pending application Ser. No. 12/613,808 entitled "Multi-Channel Detector Assembly for Downhole Spectroscopy"). When received, the control signals can configure the control circuitry's operation to account for variable conditions such as a change in temperature, a change in fluid to be analyzed, a change in mode of operation to be used, etc.

In addition to external control, the control circuitry 500 can use data from the inputs 552/556 as part of an automated control scheme. Digital signals from the digital input 552 may be used directly by the processing circuitry 520 in the automated control scheme. For analog signals, the conversion circuitry 540 interposed between the processing circuitry 520 and the input/output interface 550 uses analog-to-digital conversion (ADC) to convert the analog signals from the analog input 556 into digital signals for the processing circuitry 520 to process. The signals can include amplitude measurements used for feedback or can include analog control signals for manual or automated control of the circuitry's operation.

In one example, the inputs 552/556 can receive amplitude measurements from the reference channel and can use these measurements to control the operation of the source 510. In such a situation, the inputs 552/556 can receive amplitude measurements from a detector (not shown) configured to detect optical signals of the reference channel (150). Using those amplitude measurements as feedback, the control circuitry 500 can then control the source 510. For example, the control circuitry 500 can use amplitude measurements received via the input 552/556 for the reference channel as feedback to control the source 510 so the control circuitry 500 can maintain a more uniform intensity profile for the source 510 even when there are significant changes in environmental conditions. In particular, the preferred processing circuitry 520 drives the source 510 to maintain a relatively flat illumination profile across the entire temperature range using pulse width modulation of the drive signals for the source 510.

In another example, the inputs 552/556 can receive amplitude measurements from a detector (not shown) configured to detect optical signals of the measurement channel (140). The control circuitry 500 can use the measurements to dynamically scale the measurement channel (140) with the reference channel (150). In this way, the control circuitry 500 can use amplitude measurements from the two channels (140/150) to provide dynamic real-time scaling of the spectral output from the multiple sources 510 and to directly reference each individual spectral channel from the sources 510. Finally, using the measurements from both channels (140/150), the control circuitry 500 can correlate the measurement and reference channel data.

In addition to controlling the source 510, it will be appreciated that the control circuitry 500 can include electronic components to operate a scanning optic (as in FIG. 3B). The control circuitry 500 can function on its own independent of any measurements made of the sample fluid by a detection unit (not shown), such as disclosed in incorporated co-pending application Ser. No. 12/613,808 entitled "Multi-Channel Detector Assembly for Downhole Spectroscopy." Alternatively, the control circuitry 500 can receive measurement signals from a separate detection unit (not shown) before or after any processing has been done on such signals.

The foregoing description of preferred and other embodiments is not intended to limit or restrict the scope or applicability of the inventive concepts conceived of by the Applicants. In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. An apparatus deployable downhole for fluid analysis, comprising:
   a source generating an optical signal across a spectrum of wavelengths and routing the optical signal concurrently at a same time into a reference channel and a measurement channel;
   at least one movable element having a plurality of filters distributed thereon, the filters concurrently filtering the reference and measurement channels at a same time, the at least one movable element movable to change which of the filters filter the reference and measurement channels at the same time;
   at least one drive operable to move the at least one movable element;
   control circuitry electrically coupled to the source and the at least one drive, the control circuitry controlling illumination of the source and movement of the at least one movable element; and
   a detection unit concurrently detecting at a same time (a) the reference channel, after interaction with one of the filters of the at least one movable element, and (b) the measurement channel, after interaction with the same filter of the at least one movable element and a fluid sample,
   wherein the concurrent filtering and detection of the reference and measurement channels are matched at the same time by the same filter of the at least one movable element and account for a variable condition in the apparatus.

2. The apparatus of claim 1, wherein the source comprises one or more source elements.

3. The apparatus of claim 2, wherein the one or more source elements are selected from the group consisting of a broadband source, tungsten halogen lamp, deuterium light source, short arc Xenon light source, coiled filament Infrared (thermal) emitter, arc lamp, glow bar, metal halide lamp, a light emitting diode (LED), and a super-luminescent light emitting diode (SLED).

4. The apparatus of claim 2, wherein the source comprises a beam splitter optically coupled to the one or more source elements and fractionally splitting the optical signal from the one or more source elements concurrently into the reference and measurement channels.

5. The apparatus of claim 4, wherein the beam splitter splits the optical signal into the reference channel disproportionately compared to the measurement channel.

6. The apparatus of claim 1, wherein the at least one drive comprises at least one motor coupled to the at least one movable element.

7. The apparatus of claim 1, wherein the at least one movable element comprises at least one selective orientation permitting unfiltered passage of the measurement and reference channels.

8. The apparatus of claim 1, wherein the at least one movable element comprises at least one selective orientation completely restricting passage of the measurement and reference channels.

9. The apparatus of claim 1, wherein the at least one movable element comprises a substrate having an axis of rotation, and wherein the filters comprise a plurality of filter coatings coated onto the substrate and distributed about the axis.

10. The apparatus of claim 1, wherein the at least one movable element comprises a plurality of substrates affixed together and having an axis of rotation, and wherein the filters comprises a plurality of filter coatings coated onto the substrates and distributed about the axis.

11. The apparatus of claim 1, wherein the at least one movable element comprises a disc having an axis of rotation and defining a plurality of openings distributed about the axis, and wherein the wavelength selection filters are disposed in the openings.

12. The apparatus of claim 1, wherein the at least one movable element comprises a plurality of wheels being rotatably disposed adjacent one another, each of the wheels having a plurality of filters distributed about an axis of rotation.

13. The apparatus of claim 12, wherein the at least one drive comprises a plurality of motors each separately rotating one of the wheels.

14. The apparatus of claim 12, wherein the at least one drive comprises a single motor driving a series of the wheels with different gear ratios and having the filters selectively orientatable relative to one another.

15. The apparatus of claim 1, wherein the detection unit comprises:
   a reference detector optically coupled to the reference channel; and
   a measurement detector optically coupled to the measurement channel.

16. A downhole fluid analysis tool, comprising:
   a tool housing deployable downhole and having a flow passage for a fluid sample; and
   a fluid analysis device disposed in the tool housing relative to the flow passage, the fluid analysis device at least including
      a source generating an optical signal across a spectrum of wavelengths and routing the optical signal concurrently at a same time into a reference channel and a measurement channel,
      at least one movable element having a plurality of filters distributed thereon for concurrently filtering the reference and measurement channels at a same time, the at least one movable element being movable to change which of the filters filter the reference and measurement channels at the same time,
      at least one drive operable to rotate the at least one movable element,
      control circuitry electrically coupled to the source and the drive, the control circuitry controlling illumination of the source and movement of the at least one movable element; and
      a detection unit concurrently detecting at a same time (a) the reference channel, after interaction with one of the filters of the at least one movable element, and (b) the measurement channel, after interaction with the same filter of the at least one movable element and a fluid sample,
      wherein the concurrent filtering and detection of the reference and measurement channels are matched at the same time by the same filter of the at least one movable element and account for a variable condition in the apparatus.

17. A downhole fluid analysis method, comprising:
   deploying a fluid analysis device downhole;
   obtaining a fluid sample downhole;
   generating an optical signal across a spectrum of wavelengths;
   routing the optical signal concurrently at a same time into a reference channel and a measurement channel;

controlling orientation of a plurality of filters interposable in paths of the reference and measurement channels;

concurrently filtering the reference and measurement channels at a same time by controlling which of the filters filter the reference and measurement channels at a same time;

interacting the measurement channel with the fluid sample before or after filtering the measurement channel; and concurrently detecting the filtered reference channel and the filtered measurement channel, the detected channels being filtered by a same one of the filters interposable in the paths of the reference and measurement channels at a same time, wherein the concurrent filtering and detection of the reference and measurement channels are matched at the same time by the same filter and account for a variable condition in the apparatus.

18. The method of claim 17, wherein generating an optical signal across a spectrum of wavelengths comprises controlling illumination of one or more sources.

19. The method of claim 17, wherein routing the optical signal into a reference channel and a measurement channel comprises fractionally splitting the optical signal into the reference and measurement channels.

20. The apparatus of claim 19, wherein fractionally splitting the optical signal into the reference and measurement channels comprises splitting the optical signal into the reference channel disproportionately compared to the measurement channel.

21. The method of claim 17, wherein controlling orientation of the filters comprises driving movement of the filters with at least one motor.

22. The method of claim 17, wherein controlling orientation of the filters comprises selectively permitting unfiltered passage of the measurement and reference channels.

23. The method of claim 17, wherein controlling orientation of the filters comprises selectively restricting passage of the measurement and reference channels.

24. The method of claim 17, wherein filtering the reference and measurement channels comprises passing the channels through at least one substrate having an axis of rotation and having a plurality of filter coatings coated onto the substrate and distributed about the axis.

25. The method of claim 17, wherein filtering the reference and measurement channels comprises passing the channels through a filter optic disposed in an opening of a rotatable disc.

26. The method of claim 17, wherein filtering the reference and measurement channels comprises passing the channels through a plurality of wheels rotatably disposed adjacent one another, each of the wheels having an axis of rotation and having the filters selectively orientatable relative to one another.

27. The method of claim 17, wherein concurrently detecting the filtered reference channel and the filtered measurement channel comprises:

detecting the filtered reference channel with a reference detector optically coupled thereto; and detecting the filtered measurement channel with a measurement detector optically coupled thereto.

* * * * *